US012802825B2

(12) United States Patent
Mazumder et al.

(10) Patent No.: US 12,802,825 B2
(45) Date of Patent: Nov. 17, 2026

(54) SYSTEM AND METHOD FOR PERSONALIZATION OF CARDIAC HEMODYNAMIC DIGITAL TWIN USING ECHOCARDIOGRAM-BASED APPROACH

(71) Applicant: Tata Consultancy Services Limited, Mumbai (IN)

(72) Inventors: Oishee Mazumder, Kolkata (IN); Ayan Mukherjee, Kolkata (IN); Aniruddha Sinha, Kolkata (IN); Sundeep Khandelwal, Uttar Pradesh (IN); Shilajit Banerjee, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 137 days.

(21) Appl. No.: 19/045,306

(22) Filed: Feb. 4, 2025

(65) Prior Publication Data

US 2025/0259752 A1 Aug. 14, 2025

(30) Foreign Application Priority Data

Feb. 9, 2024 (IN) ............................ 202421008981

(51) Int. Cl.
*G16H 50/50* (2018.01)
*G06T 7/00* (2017.01)
*G16H 30/40* (2018.01)

(52) U.S. Cl.
CPC ........... *G16H 50/50* (2018.01); *G06T 7/0012* (2013.01); *G16H 30/40* (2018.01); *G06T 2207/30048* (2013.01)

(58) Field of Classification Search
CPC ........ G16H 50/50; G16H 30/40; G16H 50/20; G06T 7/0012; G06T 2207/30048; A61B 5/02028; A61B 8/0883
See application file for complete search history.

(56) References Cited

U.S. PATENT DOCUMENTS 10,299,862 B2 5/2019 Georgescu et al.
2016/0034665 A1 2/2016 Adirovich et al.
(Continued)

FOREIGN PATENT DOCUMENTS

WO 2015031576 A1 3/2015

OTHER PUBLICATIONS

Author: Xiangdong Zhang , Dan Wu, Fen Miao , Member, IEEE, Hao Liu, and Ye Li , Senior Member, IEEE Title: Personalized Hemodynamic Modeling of the Human Cardiovascular System: A Reduced-Order Computing Model Title of the item: IEEE Transactions on Biomedical Engineering Date: vol. 67, No. 10, pp., p. 2754-p. 2764.

(Continued)

*Primary Examiner* — Ming Y Hon
(74) *Attorney, Agent, or Firm* — Finnegan, Henderson, Farabow, Garrett & Dunner, LLP

(57) ABSTRACT

Existing techniques fail to propose a method for improving model parameters optimization and seamless integration of clinical data with computational model required for personalized cardiac hemodynamic model development. This disclosure relates to a system and method, which receives one or more model parameters comprising height, active pressure components and passive pressure components specific to left ventricle from cardiac hemodynamic model. The first set of values corresponding to one or more input parameters comprising end systolic diameter and end diastole diameter are received from subject specific Echo data. The second set of values corresponding to one or more model parameters are estimated using one or more input parameters. The estimated second set of values are optimized using a Particle swarm optimization to obtain one or more optimized values. Select at least a subset of optimized one or more values (Continued)

corresponding to one or more model parameters for personalization.

3 Claims, 14 Drawing Sheets

(56) References Cited

U.S. PATENT DOCUMENTS

| | | | | |
|---|---|---|---|---|
| 2016/0210435 | A1* | 7/2016 | Neumann | A61B 5/24 |
| 2016/0220311 | A1* | 8/2016 | Mansi | A61B 34/10 |
| 2020/0222607 | A1* | 7/2020 | El Katerji | A61B 5/0215 |
| 2021/0353160 | A1* | 11/2021 | Laleg | A61B 5/021 |
| 2022/0287572 | A1* | 9/2022 | Roy | A61B 5/02007 |
| 2024/0306974 | A1* | 9/2024 | Sengupta | A61B 5/341 |
| 2025/0259752 | A1* | 8/2025 | Mazumder | G16H 50/50 |

OTHER PUBLICATIONS

Author: Lucian Itu a,d,?, Puneet Sharma b, Tiziano Passerini b, Ali Kamen b, Constantin Suciu c,d, Dorin Comaniciu bTitle: A parameter estimation framework for patient-specific hemodynamic computations Title of the item: Journal of Computational Physics Date: Oct. 22, 2014 pp. 316-333.

Author: Nikolai L. Bjørdalsbakke, Jacob Sturdy, Emma M. L. Ingeström & Leif R. Hellevik Title: Monitoring variability in parameter estimates for lumped parameter models of the systemic circulation using longitudinal hemodynamic measurements Title of the item: BioMedical Engineering OnLine Date: Apr. 13, 2023.

* cited by examiner

A estimating, via the one or more hardware processors, a second set of values corresponding to (i) the height of the left ventricle ($h_{lv}$) using the first set of values corresponding to the one or more input parameters, which is represented by an equation -

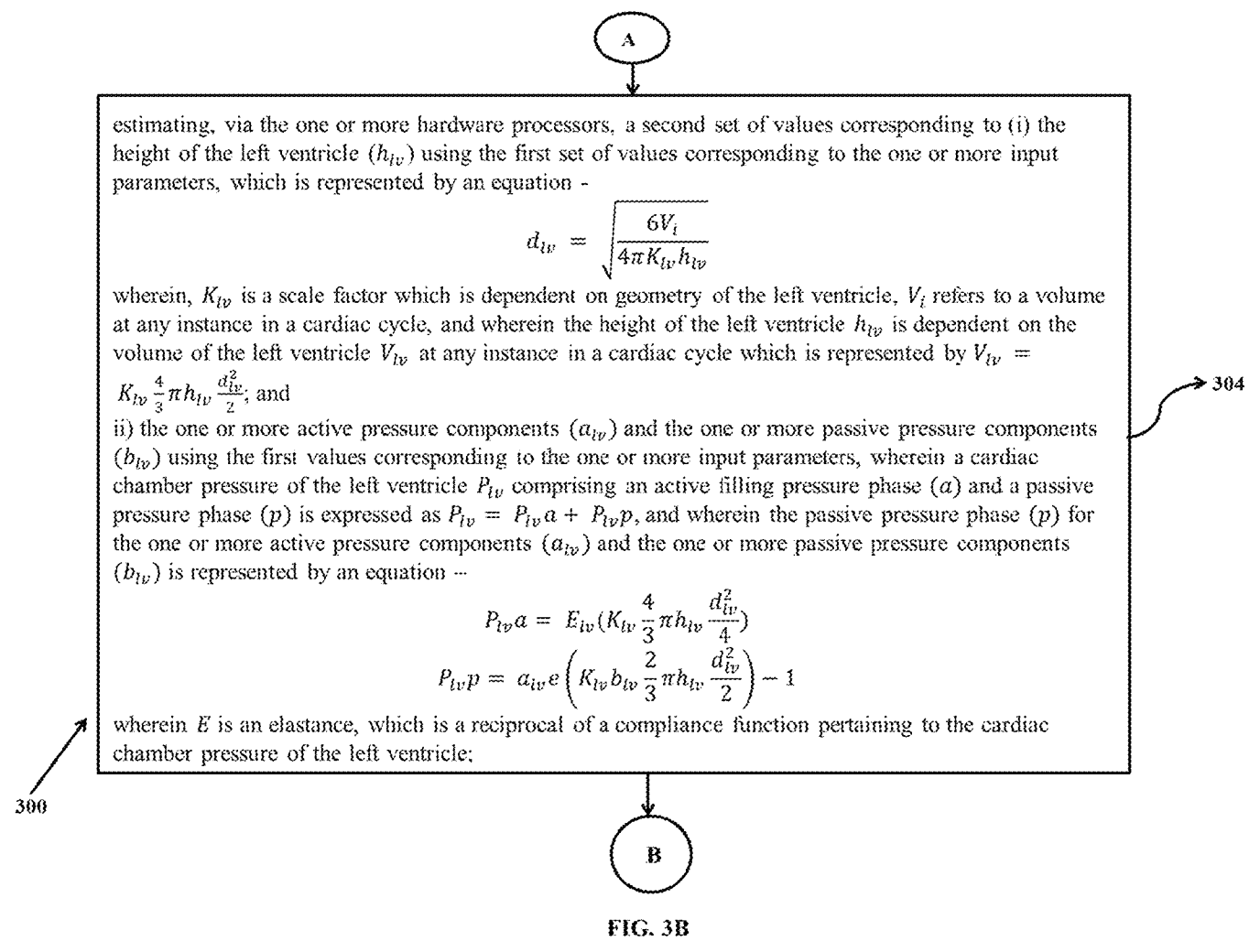

$$d_{lv} = \sqrt{\frac{6V_i}{4\pi K_{lv} h_{lv}}}$$

wherein, $K_{lv}$ is a scale factor which is dependent on geometry of the left ventricle, $V_i$ refers to a volume at any instance in a cardiac cycle, and wherein the height of the left ventricle $h_{lv}$ is dependent on the volume of the left ventricle $V_{lv}$ at any instance in a cardiac cycle which is represented by $V_{lv} = K_{lv}\frac{4}{3}\pi h_{lv}\frac{d_{lv}^2}{2}$; and ii) the one or more active pressure components ($a_{lv}$) and the one or more passive pressure components ($b_{lv}$) using the first values corresponding to the one or more input parameters, wherein a cardiac chamber pressure of the left ventricle $P_{lv}$ comprising an active filling pressure phase ($a$) and a passive pressure phase ($p$) is expressed as $P_{lv} = P_{lv}a + P_{lv}p$, and wherein the passive pressure phase ($p$) for the one or more active pressure components ($a_{lv}$) and the one or more passive pressure components ($b_{lv}$) is represented by an equation –

$$P_{lv}a = E_{lv}(K_{lv}\frac{4}{3}\pi h_{lv}\frac{d_{lv}^2}{4})$$

$$P_{lv}p = a_{lv}e\left(K_{lv}b_{lv}\frac{2}{3}\pi h_{lv}\frac{d_{lv}^2}{2}\right) - 1$$

wherein $E$ is an elastance, which is a reciprocal of a compliance function pertaining to the cardiac chamber pressure of the left ventricle;

304

300

B

FIG. 3B

SYSTEM AND METHOD FOR PERSONALIZATION OF CARDIAC HEMODYNAMIC DIGITAL TWIN USING ECHOCARDIOGRAM-BASED APPROACH

PRIORITY CLAIM

This U.S. patent application claims priority under 35 U.S.C. § 119 to: Indian Patent Application No. 202421008981, filed on Feb. 9, 2024. The entire contents of the aforementioned application are incorporated herein by reference.

TECHNICAL FIELD

The disclosure herein generally relates to personalization of cardiac hemodynamic digital twin, and, more particularly, to a system and method for personalization of cardiac hemodynamic digital twin using echocardiogram-based approach.

BACKGROUND

Personalized cardiac models replicating cardiac functionality like a 'digital twin', can serve in multiple clinical and research requirements dealing with pre-surgical planning to predictive analysis. Digital twin of human organs replicates the functionality of that organ, thereby generating synthetic process data with pathophysiological interpretability and provide a platform to simulate and analyze predictive 'what if' conditions. Cardiovascular research has long shown interest and involvement in simulating cardiac behavior in computational models. Flow models capturing hemodynamics, electrophysiology model and computational fluid dynamic (CFD) models are the functional models used to develop cardiac digital twin. These models have the capability of enhancing diagnosis of cardiovascular diseases along with the development of medical devices.

Although the importance and scope of application are huge for cardiac digital twin, the real benefit of such cardiac digital twin models in clinical applications lies in generating patient specific or personalized model that can fully replicate the condition of a given subject. Patient specific or personalized modelling involves integration and tuning of clinical data and prior physiological information in a generic computational model to enable individualized predictions and decisions. Personalized modelling in cardiac domain mostly concentrates on personalizing the hemodynamic functionality for complete cardiovascular circulation in varying degree of complexity, from zero-dimensional (OD) lumped models to three-dimensional (3D) CFD models.

The golden standard of personalized quantitative hemodynamic modelling is via CFD models that integrate cardiac structure using high resolution 3d medical images like computed tomography (CT) or magnetic resonance imaging (MRI). Based on person specific precise cardiac structure and vessel anatomy, reconstruction of flow inside cardiac substructures is modelled. Even though such models are capable of estimating cardiac metrics non-invasively, they are very computationally expensive. Reduced order models are widely used for generating hemodynamic functionality at a low computational complexity. Still, there is lack of a personalized lumped hemodynamic model for clinical applications. This is mainly due to the exceedingly large number of dependent and independent model parameters in lumped models that are required to be tuned from limited metrics available in conventional clinical data. Specialized tuning methods are used for fitting model parameters using constrained parameter estimation coupled with immense manual tuning.

SUMMARY

Embodiments of the present disclosure present technological improvements as solutions to one or more of the above-mentioned technical problems recognized by the inventors in conventional systems. For example, in one embodiment, a method for personalization of cardiac hemodynamic digital twin using echocardiogram-based approach is provided. The method includes receiving, via one or more hardware processors, (i) one or more model parameters specific to a left ventricle from a cardiac hemodynamic model, wherein the one or more model parameters specific to the left ventricle comprises height of the left ventricle ($h_{lv}$), one or more active pressure components ($a_{lv}$), one or more passive pressure components ($b_{lv}$) and one or more compliance parameters $C_{lv}$, and wherein the cardiac hemodynamic model is driven using an echocardiogram (ECG) data specific to a subject; and (ii) a first set of values corresponding to one or more input parameters from an echo data specific to the subject, wherein the one or more input parameters comprises an end systolic diameter, an end diastole diameter, an end systolic volume and an end diastolic volume specific to the left ventricle; estimating, via the one or more hardware processors, a second set of values corresponding to (i) the height of the left ventricle ($h_{lv}$) using the first set of values corresponding to the one or more input parameters, which is represented by an equation—

$$d_{lv} = \frac{6V_i}{4\pi K_{lv} h_{lv}}$$

wherein, $K_{lv}$ is a scale factor which is dependent on geometry of the left ventricle, $V_i$ refers to a volume at any instance in a cardiac cycle, and wherein the height of the left ventricle $h_{lv}$ is dependent on the volume of the left ventricle $V_{lv}$ at any instance in a cardiac cycle which is represented by $V_{lv}=$ $$K_{lv}\frac{4}{3}\pi h_{lv}\frac{d_{lv}^2}{2};$$

and ii) the one or more active pressure components ($a_{lv}$) and the one or more passive pressure components ($b_{lv}$) using the first set of values corresponding to the one or more input parameters, wherein a cardiac chamber pressure of the left ventricle $P_{lv}$ comprising an active filling pressure phase (a) and a passive pressure phase (p) is expressed as $P_{lv}=P_{lv}a+P_{lv}p$, and wherein the passive pressure phase (p) for the one or more active pressure components ($a_{lv}$) and the one or more passive pressure components ($b_{lv}$) is represented by an equation—

$$P_{lv}a = E_{lv}\left(K_{lv}\frac{4}{3}\pi h_{lv}\frac{d_{lv}^2}{4}\right)$$

$$P_{lv}p = a_{lv}e\left(K_{lv}b_{lv}\frac{2}{3}\pi h_{lv}\frac{d_{lv}^2}{2}\right) - 1$$

wherein E is an elastance, which is a reciprocal of a compliance function pertaining to the cardiac chamber pressure of the left ventricle; optimizing, via the one or more hardware processors, the estimated second set of values corresponding to the one or more model parameters using a particle swarm optimization (PSO) technique to obtain one or more optimized values, wherein the optimization is performed by comparing the estimated second set of values corresponding to the one or more model parameters with the first set of values corresponding to the one or more input parameters; and selecting, via the one or more hardware processors, at least a subset of the one or more optimized values corresponding to the one or more model parameters for personalization.

In another aspect, a system for personalization of cardiac hemodynamic digital twin using echocardiogram-based approach is provided. The system comprises: a memory storing instructions; one or more communication interfaces; and one or more hardware processors coupled to the memory via the one or more communication interfaces, wherein the one or more hardware processors are configured by the instructions to: receive (i) one or more model parameters specific to a left ventricle from a cardiac hemodynamic model, wherein the one or more model parameters specific to the left ventricle comprises height of the left ventricle ($h_{lv}$), one or more active pressure components ($a_{lv}$), one or more passive pressure components ($b_{lv}$) and one or more compliance parameters $C_{lv}$, and wherein the cardiac hemodynamic model is driven using an echocardiogram (ECG) data specific to a subject; and (ii) a first set of values corresponding to one or more input parameters from an echo data specific to the subject, wherein the one or more input parameters comprises an end systolic diameter, an end diastole diameter, an end systolic volume and an end diastolic volume specific to the left ventricle. The system further includes estimates a second set of values corresponding to (i) the height of the left ventricle ($h_{lv}$) using the first set of values corresponding to the one or more input parameters, which is represented by an equation—

$$d_{lv} = \sqrt{\frac{6V_i}{4\pi K_{lv}h_{lv}}}$$

wherein, $K_{lv}$ is a scale factor which is dependent on geometry of the left ventricle, $V_i$ refers to a volume at any instance in a cardiac cycle, and wherein the height of the left ventricle $h_{lv}$ is dependent on the volume of the left ventricle $V_{lv}$ at any instance in a cardiac cycle which is represented by $$V_{lv} = K_{lv}\frac{4}{3}\pi h_{lv}\frac{d_{lv}^2}{4};$$

and ii) the one or more active pressure components ($a_{lv}$) and the one or more passive pressure components ($b_{lv}$) using the first set of values corresponding to the one or more input parameters, wherein a cardiac chamber pressure of the left ventricle $P_{lv}$ comprising an active filling pressure phase (a) and a passive pressure phase (p) is expressed as $P_{lv}=P_{lv}a+P_{lv}p$, and wherein the passive pressure phase (p) for the one or more active pressure components ($a_{lv}$) and the one or more passive pressure components ($b_{lv}$) is represented by an equation—

$$P_{lv}a = E_{lv}\left(K_{lv}\frac{4}{3}\pi h_{lv}\frac{d_{lv}^2}{4}\right)$$

-continued $$P_{lv}p = a_{lv}e\left(K_{lv}b_{lv}\frac{2}{3}\pi h_{lv}\frac{d_{lv}^2}{2}\right) - 1$$

wherein E is an elastance, which is a reciprocal of a compliance function pertaining to the cardiac chamber pressure of the left ventricle; optimizing the estimated second set of values corresponding to the one or more model parameters using a particle swarm optimization (PSO) technique to obtain one or more optimized values, wherein the optimization is performed by comparing the estimated second set of values corresponding to the one or more model parameters with the first set of values corresponding to the one or more input parameters; and selecting at least a subset of the one or more optimized values corresponding to the one or more model parameters for personalization.

In yet another aspect, there are provided one or more non-transitory machine-readable information storage mediums comprising one or more instructions which when executed by one or more hardware processors cause receiving (i) one or more model parameters specific to a left ventricle from a cardiac hemodynamic model, wherein the one or more model parameters specific to the left ventricle comprises height of the left ventricle ($h_{lv}$), one or more active pressure components ($a_{lv}$), one or more passive pressure components ($b_{lv}$) and one or more compliance parameters $C_{lv}$, and wherein the cardiac hemodynamic model is driven using an echocardiogram (ECG) data specific to a subject; and (ii) a first set of values corresponding to one or more input parameters from an echo data specific to the subject, wherein the one or more input parameters comprises an end systolic diameter, an end diastole diameter, an end systolic volume and an end diastolic volume specific to the left ventricle; estimating a second set of values corresponding to (i) the height of the left ventricle ($h_{lv}$) using the first set of values corresponding to the one or more input parameters, which is represented by an equation—

$$d_{lv} = \sqrt{\frac{6V_i}{4\pi K_{lv}h_{lv}}}$$

wherein, $K_{lv}$ is a scale factor which is dependent on geometry of the left ventricle, $V_i$ refers to a volume at any instance in a cardiac cycle, and wherein the height of the left ventricle $h_{lv}$ is dependent on the volume of the left ventricle $V_{lv}$ at any instance in a cardiac cycle which is represented by $$V_{lv} = K_{lv}\frac{4}{3}\pi h_{lv}\frac{d_{lv}^2}{4};$$

and ii) the one or more active pressure components ($a_{lv}$) and the one or more passive pressure components ($b_{lv}$) using the first set of values corresponding to the one or more input parameters, wherein a cardiac chamber pressure of the left ventricle $P_{lv}$ comprising an active filling pressure phase (a) and a passive pressure phase (p) is expressed as $P_{lv}=P_{lv}a+P_{lv}p$, and wherein the passive pressure phase (p) for the one or more active pressure components ($a_{lv}$) and the one or more passive pressure components ($b_{lv}$) is represented by an equation—

$$P_{lv}a = E_{lv}\left(K_{lv}\frac{4}{3}\pi h_{lv}\frac{d_{lv}^2}{4}\right)$$

-continued $$P_{lv}p = a_{lv}e\left(K_{lv}b_{lv}\frac{2}{3}\pi h_{lv}\frac{d_{lv}^2}{2}\right) - 1$$

wherein E is an elastance, which is a reciprocal of a compliance function pertaining to the cardiac chamber pressure of the left ventricle; optimizing the estimated second set of values corresponding to the one or more model parameters using a particle swarm optimization (PSO) technique to obtain one or more optimized values, wherein the optimization is performed by comparing the estimated second set of values corresponding to the one or more model parameters with the first set of values corresponding to the one or more input parameters; and selecting at least a subset of the one or more optimized values corresponding to the one or more model parameters for personalization.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIGS. 3A, 3B, and 3C are flow diagrams illustrating the steps involved in the method for personalization of cardiac hemodynamic digital twin using echocardiogram (ECG)-based approach, according to some embodiments of the present disclosure.

DETAILED DESCRIPTION

Figure 1:
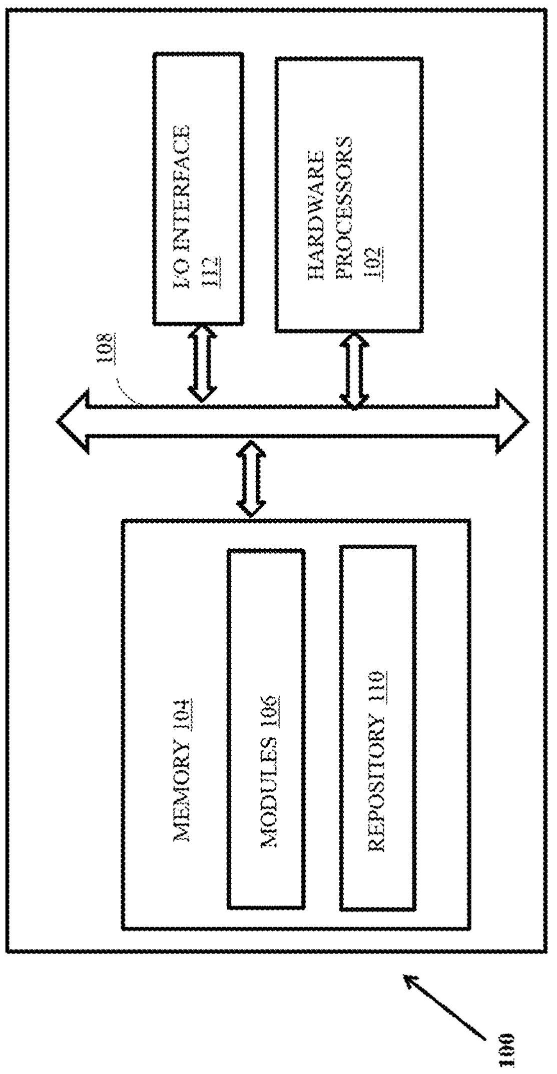
FIG. 1 illustrates an exemplary system for personalization of cardiac hemodynamic digital twin using echocardiogram-based approach, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

The present disclosure provides a system and method for personalization of cardiac hemodynamic digital twin using echocardiogram-based approach. The present disclosure proposes a particle swarm optimization (PSO) method to create a personalized cardiac hemodynamic digital twin. The proposed framework selects optimal value of cardiac chamber parameters only from echocardiogram (ECG) and an echo-doppler/echo data to tune a lumped cardiac hemodynamic model. The cardiac hemodynamic model is a closed-loop, real-time, lumped parameter cardiovascular simulation model. The cardiac hemodynamic model replicates the dynamics of four cardiac chambers, heart valves, pulmonary, and lumped systemic circulation. The pulsatile activity and cardiac chamber compliance are triggered and modulated by a patient/subject specific echocardiogram (ECG) data. Personalization of the cardiac chamber parameters including an end systolic diameter, a diastolic diameter, an end systolic volume and a diastolic volume are computed from the echo data while timing specific information of heart chamber contraction is derived from the echocardiogram (ECG).

Referring now to the drawings, and more particularly to FIG. 1 through FIG. 9B, where similar reference characters denote corresponding features consistently throughout the figures, there are shown preferred embodiments and these embodiments are described in the context of the following exemplary system and/or method.

FIG. 1 illustrates an exemplary system for personalization of cardiac hemodynamic digital twin using echocardiogram-based approach, according to some embodiments of the present disclosure. In an embodiment, the system 100 includes or is otherwise in communication with hardware processors 102, at least one memory such as a memory 104, and an I/O interface 112. The hardware processors 102, memory 104, and the Input/Output (I/O) interface 112 may be coupled by a system bus such as a system bus 108 or a similar mechanism. In an embodiment, the hardware processors 102 can be one or more hardware processors.

The I/O interface 112 may include a variety of software and hardware interfaces, for example, a web interface, a graphical user interface, and the like. The I/O interface 112 may include a variety of software and hardware interfaces, for example, interfaces for peripheral device(s), such as a keyboard, a mouse, an external memory, a printer and the like. Further, the I/O interface 112 may enable the system 100 to communicate with other devices, such as web servers, and external databases.

The I/O interface 112 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface 112 may include one or more ports for connecting several computing systems with one another or to another server computer. The I/O interface 112 may include one or more ports for connecting several devices to one another or to another server.

The one or more hardware processors 102 may be implemented as one or more microprocessors, microcomputers, microcontrollers, digital signal processors, central processing units, node machines, logic circuitries, and/or any devices that manipulate signals based on operational instructions. Among other capabilities, the one or more hardware processors 102 is configured to fetch and execute computer-readable instructions stored in memory 104.

The memory 104 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. In an embodiment, the memory 104 includes a plurality of modules 106. The memory 104 also includes a data repository (or repository) 110 for storing data processed, received, and generated by the plurality of modules 106.

The plurality of modules 106 includes programs or coded instructions that supplement applications or functions performed by the system 100 for personalization of cardiac hemodynamic digital twin using echocardiogram-based approach. The plurality of modules 106, amongst other things, can include routines, programs, objects, components, and data structures, which perform particular tasks or implement particular abstract data types. The plurality of modules 106 may also be used as signal processor(s), node machine (s), logic circuitries, and/or any other device or component that manipulates signals based on operational instructions. Further, the plurality of modules 106 can be used by hardware, by computer-readable instructions executed by the one or more hardware processors 102, or by a combination thereof. The plurality of modules 106 can include various sub-modules (not shown). The plurality of modules 106 may include computer-readable instructions that supplement applications or functions performed by the system 100 for personalization of cardiac hemodynamic digital twin using echocardiogram based approach. In an embodiment, the modules 106 include a cardiac hemodynamic model 202, a left ventricle model parameters module 204, an echo data module 206, a particle swarm optimization (PSO) module 208, an optimized model parameters module 210 and a personalized hemodynamic model 212. The modules are depicted in FIG. 2.

The data repository (or repository) 110 may include a plurality of abstracted pieces of code for refinement and data that is processed, received, or generated as a result of the execution of the module(s) 106.

Although the data repository 110 is shown internal to the system 100, it will be noted that, in alternate embodiments, the data repository 110 can also be implemented external to the system 100, where the data repository 110 may be stored within a database (repository 110) communicatively coupled to the system 100. The data contained within such an external database may be periodically updated. For example, new data may be added into the database (not shown in FIG. 1) and/or existing data may be modified and/or non-useful data may be deleted from the database. In one example, the data may be stored in an external system, such as a Lightweight Directory Access Protocol (LDAP) directory and a Relational Database Management System (RDBMS).

Figure 2:
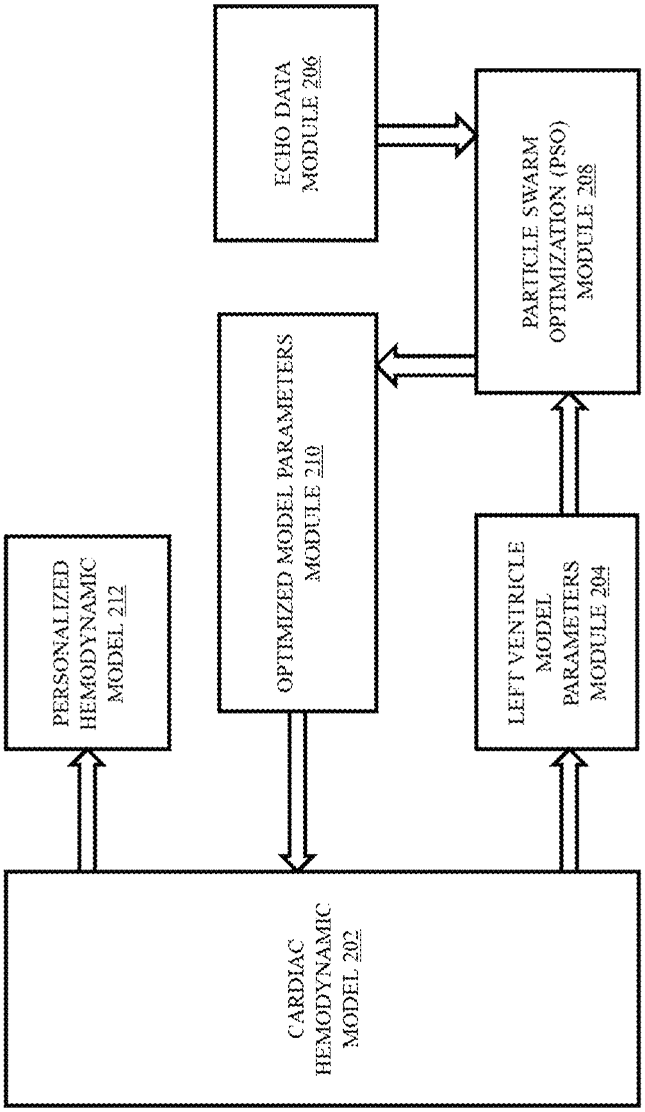
FIG. 2 is a functional block diagram of the system for personalization of cardiac hemodynamic digital twin using echocardiogram-based approach, according to some embodiments of the present disclosure.
Figure 3A:
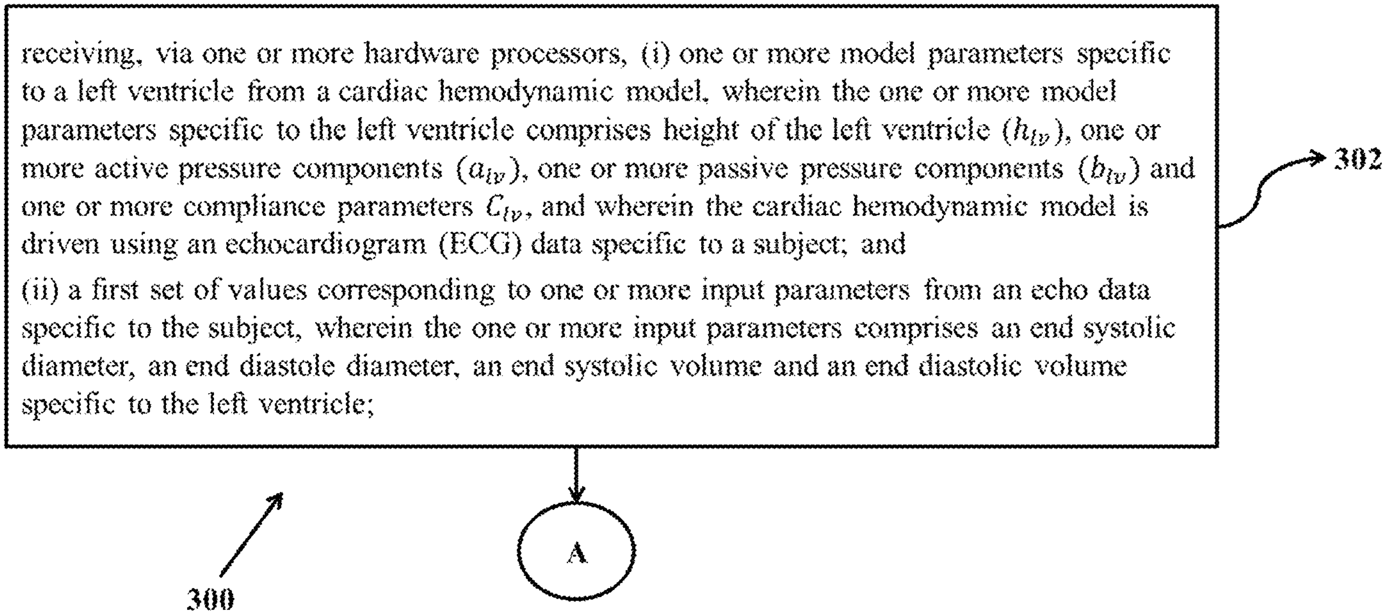
Figure 3C:
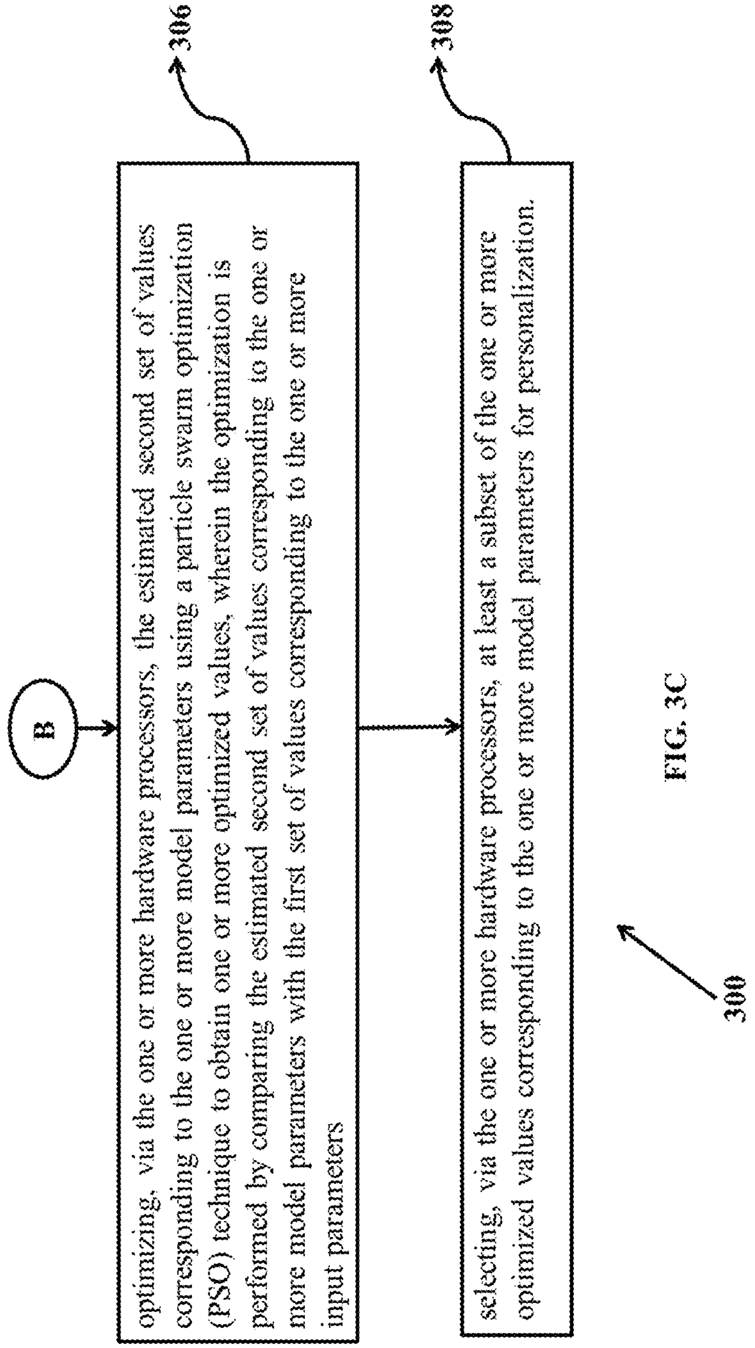

FIGS. 3A through 3C are flow diagrams illustrating a method for personalization of cardiac hemodynamic digital twin using echocardiogram-based approach using the systems 100 of FIGS. 1-2, according to some embodiments of the present disclosure. Steps of the method of FIGS. 3A through 3C shall be described in conjunction with the components of FIG. 2. At step 302 of the method 300 of the present disclosure, the one or more hardware processors 102 receive one or more model parameters specific to a left ventricle from a cardiac hemodynamic model represented by the cardiac hemodynamic model 202. The cardiac hemodynamic model is a closed-loop, real-time, lumped parameter cardiovascular simulation model. The cardiac hemodynamic model replicates the dynamics of four cardiac chambers, heart valves, pulmonary, and lumped systemic circulation. The pulsatile activity and cardiac chamber compliance are triggered and modulated using patient/subject specific echocardiogram (ECG) data. In an embodiment of the present disclosure, the one or more model parameters specific to the left ventricle (represented by the left ventricle model parameters module 204) comprises height of the left ventricle ($h_{lv}$), one or more active pressure components ($a_{lv}$), one or more passive pressure components ($b_{lv}$) and one or more compliance parameters $C_{lv}$. Further a first set of values corresponding to one or more input parameters are received from an echo data (represented by the echo data module 206) specific to the subject. In an embodiment of the present disclosure, the one or more input parameters comprises an end systolic diameter, an end diastole diameter, an end systolic volume, an end diastolic volume specific to the left ventricle.

Figure 5:
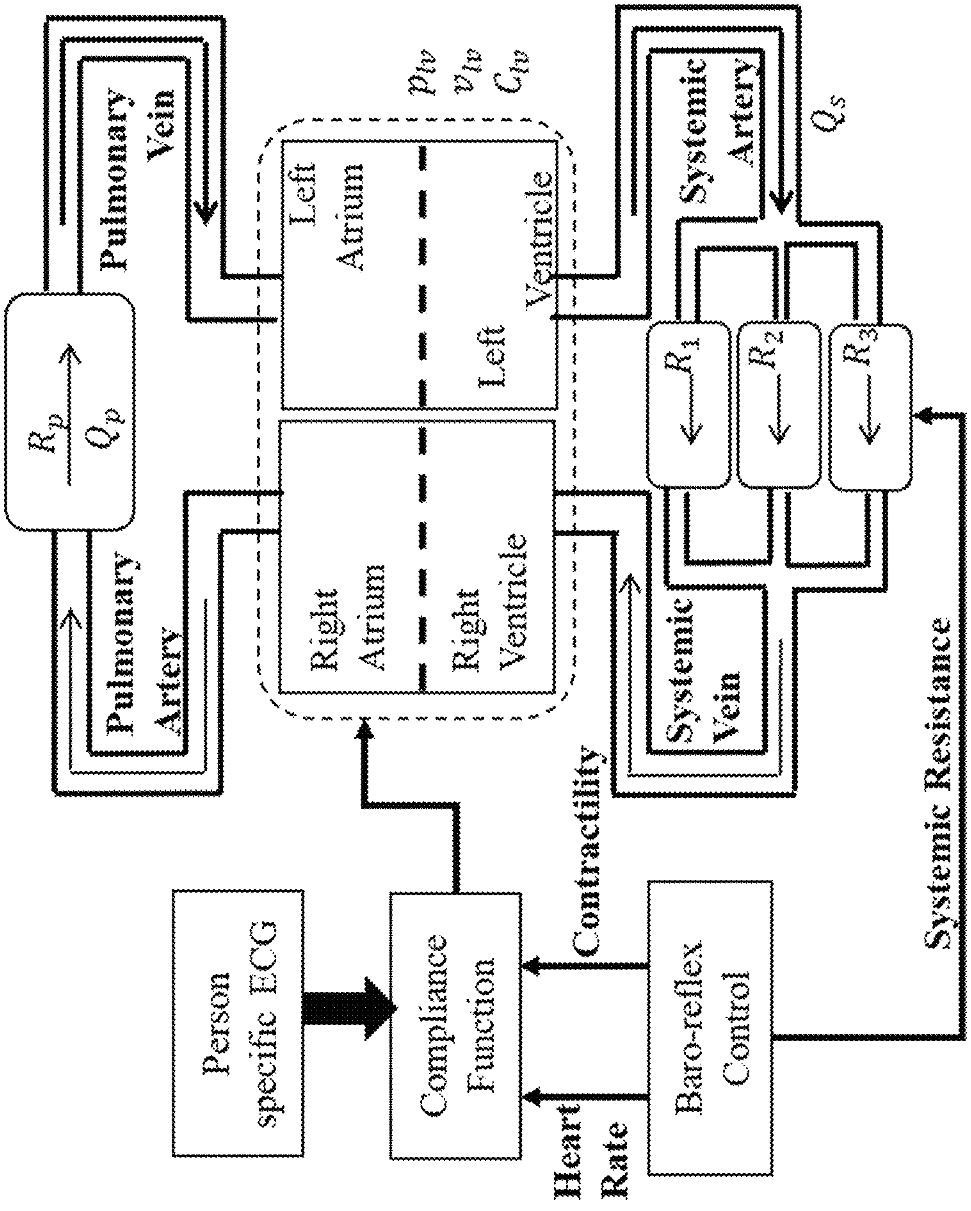
FIG. 5 is a schematic representation of the cardiac hemodynamic model in accordance with some embodiments of the present disclosure.

The developed cardiac hemodynamic model is a Od model comprising of a multi-chambered heart (e.g., 4 chambers) with proper valve functioning and lumped systemic and pulmonary circulation. The pulsatile cardiac behavior is triggered using echocardiogram (ECG), which drives the cardiac hemodynamic model to generate the pressure volume dynamics during different cardiac phases. Opening and closing of cardiac valves (e.g., mitral, aortic valves in the left heart and tricuspid, pulmonic valves in the right heart) are modelled in synchronous with the pressure difference within the heart chambers to ensure unidirectional blood flow. The cardiac chambers are modelled by pressure and volume related components to incorporate both active and passive filling phases resulting in more realistic changes of filling pressures with ventricular dilatation. Heart rate, contractility, and systemic resistance are controlled through a baroreflex controller that autoregulates blood pressure. The schematic representation of the cardiac hemodynamic model is shown in FIG. 5. 'Q', 'R' indicates flow and resistance, Suffix 's' represents systemic flow, 'p' represents pulmonary flow. Pressure, volume and compliance specific to the left ventricle are indicated as $p_{lv}$, $v_{lv}$, $C_{lv}$ respectively. For personalization, $C_{lv}$ parameters are derived from ECG while parameters for $v_{lv}$ and $p_{lv}$ are derived from the echo data.

Pumping actions of the heart chambers are activated sequentially by time-varying compliance function (C(t)) derived from person specific echocardiogram (ECG) signal. Initiation of the pumping action starts from Sino-atrial (SA) node and travels to left atrium (la) with a delay of dla unit (delay from the left atrium to the left ventricle), bringing in atrial contraction that pumps blood to the left ventricle. The activation then passes to atrio-ventricular (AV) node with a delay of d unit, allowing the ventricles to fill with blood. The left ventricle compliance function $C_{lv}$ can be expressed as $$C_{lv}(t) = C_{lv} * u_v(t-d) \tag{1}$$

$$u_v(t) = \begin{cases} 5 - 0.5\cos\left(\pi \frac{t}{T_1}\right), & 0 \le t < T_1 \\ 0.5 + 0.5\cos\left(\pi \frac{t - T_1}{T_2 - T_1}\right), & T_1 \le t < T_2 \\ 0, & T_2 \le t < T \end{cases} \tag{2}$$

where $C_{lv}$ is the compliance across lv, $u_v(t)$ is the activation function, d represents the delay in activation of lv from ra (right atrium), t is any point in the cardiac cycle.

$$T\left(=\frac{60}{HR}\right)$$

is the duration of the cardiac cycle (HR is the Heart Rate) and T1 and T2 are the systolic and diastolic activation time instances of the cardiac cycle (T). Delays are computed from time axis of occurrence of PQRST parameters of the ECG wave, while amplitude of activation is modulated from the ratio of depolarization to repolarization for atrium and ventricles. The left ventricle compliance (equation. 1) is thus computed from the subject specific echocardiogram (ECG) as $C_{lv}=A_{tr}/A_{tt}$. $A_{tr}$ is the echocardiogram (ECG) wave amplitude at time instance tr, which corresponds with the R peak of the QRS complex representing ventricular depolarization. Similarly, $A_{tt}$ is the amplitude at time instance tt, corresponding to ST segment peak representing ventricular repolarization. The pressure volume dynamics of the left ventricle can be expressed as:

$$P_{lv}=\frac{1}{C_{lv}(t)}\left[U_{mi}\frac{P_{la}-P_{lv}}{R_{mi}}-U_{ao}\frac{P_{la}-P_{sa}}{R_{ao}}-C_{lv}(t)P_{lv}\right] \tag{3}$$

where $C_{lv}$ is the lv compliance computed previously from echocardiogram (ECG), $P_{la}$, $P_{lv}$, $P_{sa}$ are the pressure variables in the la, lv, systemic arteries (sa) respectively. $R_{mi}$, $R_{ao}$ are the valvular resistance across the mitral and aortic valves. The cardiac chambers are considered compliance vessels, and the blood vessels are considered resistive in nature. $U_{mi}$ and $U_{ao}$ are the control inputs for opening and closing of the heart valves. Those functionalities are defined as $$U_{mi}=\begin{cases}1-R_{mi}, & \text{if, } P_{la}>P_{lv};\\ \delta_{mi}, & \text{otherwise}\end{cases} \tag{4}$$

$$U_{ao}=\begin{cases}1-R_{ao}, & \text{if, } P_{lv}>P_{sa};\\ \delta_{ao}, & \text{otherwise}\end{cases} \tag{5}$$

where $(1-R_{mi})$ and $(1-R_{mi})$ represent the effective opening of the valves. For healthy condition $R_{mi}$ and $R_{ao}$ are 0. $\delta_i$; $\forall i\in\{mi, ao\}$ defines closing of the cardiac valves. In healthy cardiac condition, $\delta_i=0$.

The parameter $V_{lv}$ can be evaluated as:

$$V_{lv}=C_{lv}(t)P_{lv}+C_{lv}(t)P_{lv} \tag{6}$$

At step 304 of the method 300, the one or more hardware processors 102 estimate a second set of values corresponding to the height of the left ventricle ($h_{lv}$), the one or more active pressure components ($a_{lv}$) and the one or more passive pressure components ($b_{lv}$) using the first set of values corresponding to the one or more input parameters. Further the one or more active pressure components ($a_{lv}$) and the one or more passive pressure components ($b_{lv}$) are estimated using the one or more input parameters.

Estimating Cardiac Chamber parameters: Cardiac chamber parameters are dependent on $C_{lv}$ (equation (1), equation (2)) (derived from ECG) $P_{lv}$ (equation (3)) and $V_{lv}$ (equation (6)) parameters. For personalization, cardiac chamber diameter needs to be estimated which in turn is dependent on volume of the cardiac chambers. Considering shape of the heart chambers to be ellipsoidal, diameter of left ventricle $d_{lv}$ can be calculated from the simulated volumes as $$d_{lv}=\sqrt{\frac{6V_i}{4\pi K_{lv}h_{lv}}} \tag{7}$$

wherein, $K_{lv}$ is a scale factor dependent on geometry of the left ventricle and $V_i$ refers to volume at each instance of time. The term ($h_{lv}$) is again dependent on chamber volume as:

$$V_{lv}=K_{lv}\frac{4}{3}\pi h_{lv}\frac{d_{lv}^2}{2}.$$

Optimizing the parameter $h_{lv}$ in turn could personalize chamber dimension and volume.

Cardiac chamber pressure comprises of an active filling pressure phase (a) and passive pressure phase (p): $P_{lv}=P_{lv}a+P_{lv}p$. The active filling pressure phase (a) and the passive pressure phase (p) for the one or more active pressure components ($a_{lv}$) and the one or more passive pressure components ($b_{lv}$) is represented by an equation:

$$P_{lv}a=E_{lv}\left(K_{lv}\frac{4}{3}\pi h_{lv}\frac{d_{lv}^2}{4}\right) \tag{8}$$

$$P_{lv}p=a_{lv}e\left(K_{lv}b_{lv}\frac{2}{3}\pi h_{lv}\frac{d_{lv}^2}{2}\right)-1 \tag{9}$$

where, E is elastance which is the reciprocal of compliance function, e refers to an exponent, $a_{lv}$ and $b_{lv}$ are active pressure components and passive pressure components respectively, that need to be optimized for personalization. So, the parameters for personalizing the pressure and the volume specific to the left ventricle are $h_{lv}$, $a_{lv}$ and $b_{lv}$. The echo data comprises of the end systolic diameter (ESD), the end diastolic diameter (EDD), the end systolic volume (ESV) and the diastolic volume (EDV) specific to the left ventricle. The optimization framework takes LVEDD (left ventricle end systolic diameter), LVESD (left ventricle end diastolic diameter), LVESV (left ventricle end systolic volume) and LVEDV (left ventricle end systolic volume) from the subject specific echo data and tries to optimize the parameters $h_{lv}$, $a_{lv}$ and $b_{lv}$.

At step 306 of the method 300, the particle swarm optimization (PSO) module 208 executed via the one or more hardware processors 102 optimizes the estimated second set of values corresponding to the one or more model parameters using the particle swarm optimization (PSO) technique to obtain one or more optimized values. The optimization is performed by comparing the estimated second set of values corresponding to the one or more model parameters with the first set of values corresponding to one or more input parameters.

At step 308 of the method 300, the optimized model parameters module 210 and the personalized hemodynamic model 212 executed via the one or more hardware processors 102 select at least a subset of the one or more optimized values corresponding to the one or more model parameters for personalization.

The particle swarm optimization (PSO) is a meta-heuristic optimization algorithm motivated by the social behavior of bird flock or fish school (known in the art). The particle swarm optimization (PSO) algorithm supports parallel computation and has fast convergence which makes it a default choice of algorithm in diverse applications ranging from bio molecular research to sensor networks. Like other meta-heuristic algorithms (known in the art), PSO generates, operates, and refines candidate solutions (particles) to arrive at the optimized values of the target parameters. The movement of the particles are a function of the individual best-known positions as well as the complete swarm's best-known position. Algorithm parameters involved in PSO are Position of the particle or agent ($x_i$), Velocity of the particle or agent ($v_i$), Population of agents (A), Inertia weight (W), Cognitive constant (C1), Random numbers (R1, R2) and social constant (C2). The quality of the candidate solutions is quantified based on the user-defined objective function $f(x)$, where x is the parameter vector to be optimized. The objective function formulated for the current application is given in equation. (10).

$$f(x)=\sum_{i=1}^{N}\lambda_1\frac{x_i-x_i^{target}}{x_i^{target}} \tag{10}$$

In equation. (10), $$x_i^{target}$$

is the target value of the $i_{th}$ parameter, $x_i$ is the $i_{th}$ element of the solution candidate and $\lambda_i$ is the regularization parameter for the $i_{th}$ variable, N is the number of targets (4 in this case, However, such value of the number of targets shall not be construed as limiting the scope of the present disclosure). The objective function is defined as the summation of the absolute error percentage with respect to the target variables. Therefore, as PSO navigates the particle search space minimizing $f(x)$, the over-all cumulative absolute error is minimized. Further, four regularization parameters ($\lambda_i$) are present for modulating the weights of the error components. For the present case, $\lambda_i=1$, $\forall i$. The elements of x are LVEDD, LVESD, LVEDV and LVESV, which are the target parameters to optimize the variables $h_{lv}$, $a_{lv}$ and $b_{lv}$.

Solution space to generate the optimized values is defined by the upper and lower bounds set for these variables; bounds are 1 to 15 for $h_{lv}$ and $a_{lv}$, 0.01 to 1 for $b_{lv}$. The ranges considered for the four elements of x are LVEDD: [3,10], LVESD: [2,7], LVEDV: [90, 150] and LVESV: [40, 80]. These ranges include normal pathological range and beyond. For these defined ranges, 10 sets of target parameters are obtained by dividing the ranges linearly. The choices of the key hyperparameters are as follows: Population size: 60; Inertia weight: 2; Learning factors: (2,2); Max Stall iterations: 2; Max iteration: 25. Under this setting, the PSO based framework is run for all the 10 sets of target vectors. The progression of the objective function for the runs is plotted in FIGS. 6A and 6B. From the plot the efficacy of the PSO framework can be traced for each iteration.

Figure 4:
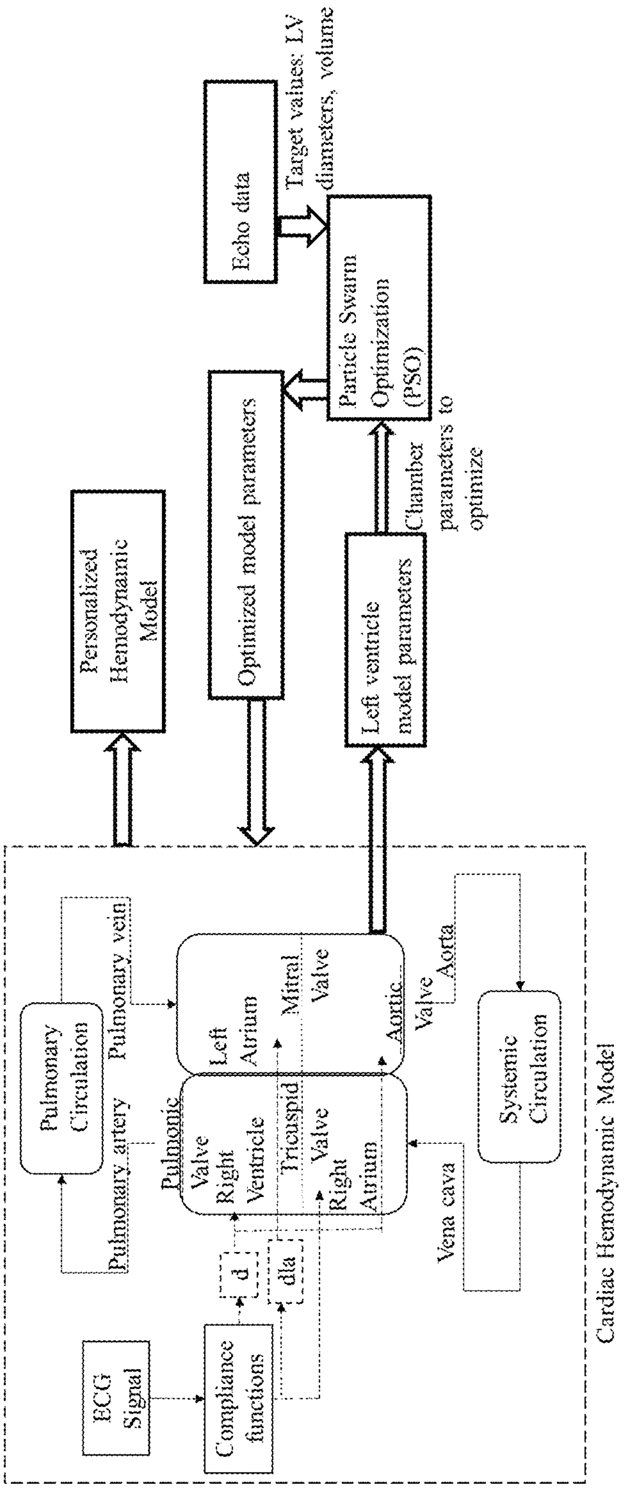
FIG. 4 is a block diagram illustrating a framework to personalize cardiac hemodynamic model according to some embodiments of the present disclosure.

FIG. 4 is a block diagram illustrating a framework to personalize cardiac hemodynamic model according to some embodiments of the present disclosure. In an embodiment of the present disclosure, the cardiac hemodynamic model is driven using the subject specific echocardiogram (ECG) which computes a chamber compliance and an activation. From the cardiac hemodynamic model, the one or more model parameters specific to the left ventricle that needs to be personalized, including chamber dimension, specifically the height of left ventricle $h_{lv}$, the one or more active pressure components ($a_{lv}$) and the passive pressure components ($b_{lv}$) are fed to the particle swarm optimization framework (PSO) framework. The one or more input parameters for optimizing the one or more model parameters are the end diastolic diameter, the end systolic diameter, the end systolic volume and the end diastolic volume specific to the left ventricle. These values are directly fed from the subject specific echo data. The optimized left ventricle chamber parameters (one or more model parameters) generated by the PSO framework are used to tune the cardiac hemodynamic model into a personalized model.

FIG. 5 is a schematic representation of the cardiac hemodynamic model in accordance with some embodiments of the present disclosure. The details of the cardiac hemodynamic model are explained in the previous sections.

Figure 6A:
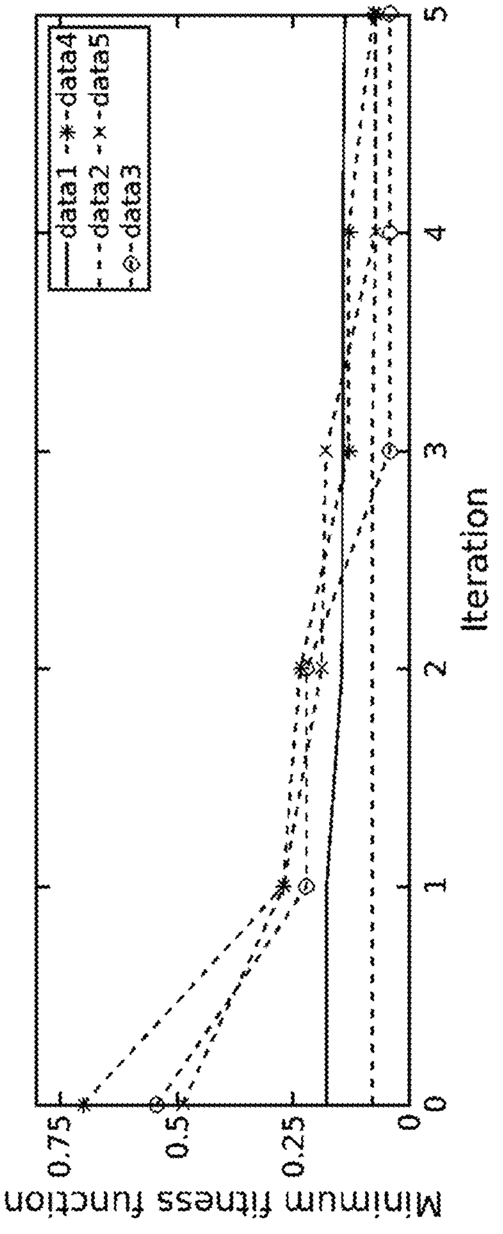
FIGS. 6A and 6B illustrate progression of an objective function value across iterations for runs of the Particle swarm optimization (PSO) framework for 10 sets of target vector, according to some embodiments of the present disclosure.
Figure 6B:
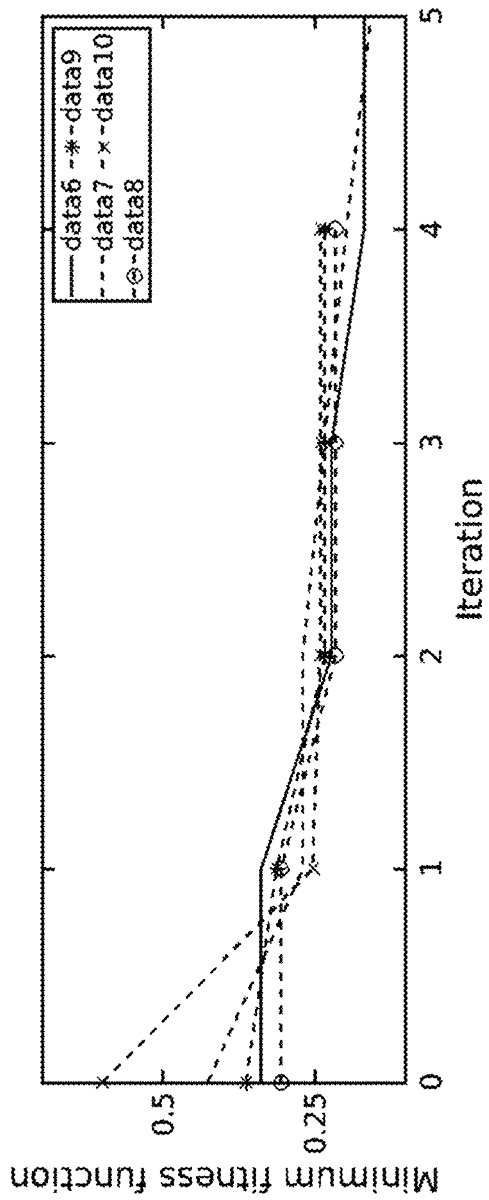

FIGS. 6A and 6B illustrate progression of an objective function value across iterations for runs of the particle swarm optimization (PSO) framework for 10 sets of target vector, according to some embodiments of the present disclosure.

The framework of the present disclosure has been tested for optimizing left ventricle chamber parameters including chamber dimension and pressure variables for a range of the end systolic diameter, the diastolic diameter, the end systolic volume, and the diastolic volume. Two specific personalized cardiac models, one representing a healthy subject, and the other representing a subject suffering from cardiac amyloidosis disease condition are reported. The personalized cardiac hemodynamic models of the present disclosure can provide an intuitive platform to understand disease progression and manifestation that could eventually lead to personalized surgical planning, treatment, and tailored prescription generation.

Clinically relevant metrics derived from the left ventricle are information associated with left ventricle (LV) pressure volume (PV) loop. From the PV loop, physiological parameters such as stroke volume (SV), cardiac output (CO), ejection fraction (EF), the end diastolic volume (EDV) and the end systolic volume (ESV) can be estimated (known in the art) which provide information on general working of the heart. The left ventricle (LV) parameters obtained from echo reports are LVEDD, LVESD, LVEDV, LVESV along with SV (EDV−ESV), EF ((SV/EDV)*100) and information related to valve flow, E/A ratio (known in the art), etc. The personalized cardiac hemodynamic model computes all these relevant metrics using the optimized parameters ($h_{lv}$, $a_{lv}$, $b_{lv}$) returned by the PSO framework. In the present disclosure, these metrics are reported for the healthy subject and for the subject diagnosed with cardiac amyloidosis.

Table 1 depicts the performance of the PSO framework in optimizing target variables on the specified range for a set of 10 targets. Along with the specified values of LVEDD, LVESD, LVEDV and LVESV, the present disclosure computes stroke volume (SV) and ejection fraction (EF) from the cardiac hemodynamic model using the optimized values returned by the PSO framework. The target ranges were provided around a span which captures the normal range as well as values below and above normal ranges for the left ventricle (LV) diameter and volume, which may coincide with pathological conditions. The PSO framework was able to reach targeted values within nominal error range. SV and EFE were recalculated from the cardiac hemodynamics model after fitting optimized $h_{lv}$, $a_{lv}$ and $b_{lv}$ parameters returned by the PSO framework for the given set of target values for left ventricle (LV) diameter and volume.

TABLE 1

PSO Framework Performance

| Config. | LVEDD | LVESD | LVEDV | LVESV | SV | EF |
|---|---|---|---|---|---|---|
| Target | 3.0 | 2.0 | 90.0 | 40.0 | 50.0 | 55.0 |
| Achieved | 3.09 | 2.11 | 86.67 | 40.17 | 46.2 | 53.49 |
| Error (%) | 3 | 5.5 | 4 | 0.4 | 7.6 | 2.7 |
| Target | 3.78 | 2.56 | 99.67 | 44.0 | 52.23 | 54.02 |
| Achieved | 3.65 | 2.5 | 96.08 | 45.03 | 51.05 | 53.13 |
| Error (%) | 3.4 | 2.3 | 0.6 | 1.3 | 2.3 | 1.6 |
| Target | 4.56 | 3.11 | 103.33 | 48.89 | 48.89 | 53.07 |
| Achieved | 4.49 | 3.12 | 101.22 | 49.06 | 52.16 | 51.53 |
| Error (%) | 1.5 | 0.3 | 2 | 0.3 | 1.2 | 2.9 |
| Target | 5.33 | 3.67 | 110 | 53.33 | 55.51 | 56.67 |
| Achieved | 5.47 | 3.75 | 110.17 | 51.75 | 58.42 | 53.03 |
| Error (%) | 2.6 | 2.2 | 0.2 | 3 | 5.2 | 6.4 |
| Target | 6.11 | 4.22 | 116.67 | 57.78 | 58.89 | 54.44 |
| Achieved | 6.17 | 4.21 | 121.54 | 56.63 | 64.91 | 53.41 |
| Error (%) | 1.0 | 0.2 | 4.2 | 2.0 | 10.2 | 1.9 |
| Target | 6.89 | 4.78 | 123.33 | 62.22 | 61.11 | 50.15 |
| Achieved | 6.89 | 4.64 | 129.09 | 62.90 | 66.19 | 51.27 |
| Error (%) | 0 | 2.9 | 4.7 | 1.1 | 8.3 | 2.2 |
| Target | 7.67 | 5.33 | 130.0 | 66.67 | 63.33 | 57.77 |
| Achieved | 7.66 | 5.17 | 132.66 | 60.54 | 72.12 | 54.36 |
| Error (%) | 0.1 | 3 | 2.0 | 9.2 | 13.9 | 5.9 |
| Target | 8.44 | 5.89 | 136.67 | 71.11 | 65.66 | 53.21 |
| Achieved | 8.9 | 5.96 | 138.05 | 66.39 | 71.66 | 51.91 |
| Error (%) | 5.5 | 1.2 | 1.0 | 6.6 | 9.1 | 2.4 |
| Target | 9.22 | 6.44 | 143.33 | 75.56 | 67.77 | 52.7 |
| Achieved | 9.62 | 6.4 | 145.89 | 73.5 | 72.39 | 49.62 |
| Error (%) | 4.3 | 0.6 | 1.8 | 2.7 | 6.8 | 5.8 |
| Target | 10.0 | 7.0 | 150.0 | 80.0 | 70.0 | 50.6 |
| Achieved | 10.08 | 6.71 | 158.72 | 74.66 | 84.06 | 52.96 |
| Error (%) | 0.8 | 4.1 | 5.8 | 6.7 | 20.1 | 4.7 |

Figure 7:
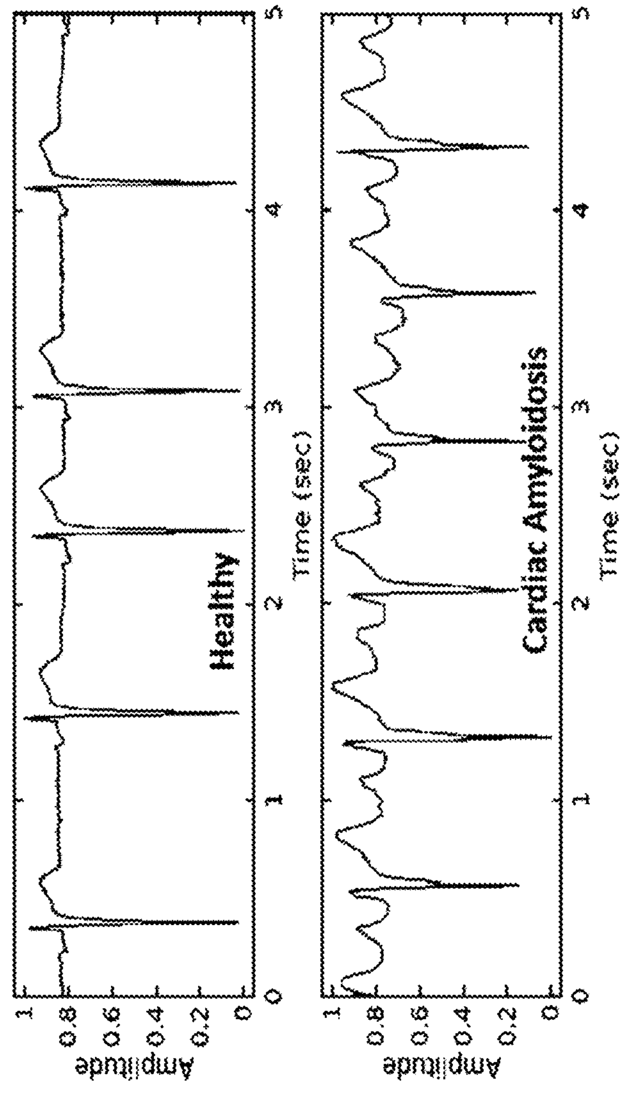
FIG. 7 illustrates an echocardiogram (ECG) timeseries for a healthy subject and a subject diagnosed with cardiac amyloidosis to drive the cardiac hemodynamic model, according to some embodiments of the present disclosure.

FIG. 7 illustrates an echocardiogram (ECG) timeseries for a healthy subject and a subject diagnosed with cardiac amyloidosis to drive the cardiac hemodynamic model, according to some embodiments of the present disclosure. In an embodiment of the present disclosure, the integrated performance of the PSO framework and the cardiac hemodynamic model are validated by directly feeding echocardiogram (ECG) and echo data of 2 subjects, one healthy and the other suffering from cardiac amyloidosis to bring in the effect of personalization. Cardiac amyloidosis is a condition where faulty proteins get deposited in cardiac structure due to protein mis-folding. This causes the left ventricle (LV) diastolic disorders and inefficient pumping, leading to heart failure (known in the art).

Normal echocardiogram (ECG) data from physio net database (known in the art) and standard healthy echo parameter ranges (known in the art) were set as target values for healthy condition. For cardiac amyloidosis, the echocardiogram (ECG) data were digitized from an echocardiogram (ECG) strip image provided (known in the art) along with the one or more input parameters received from the echo data. FIG. 7 shows echocardiogram (ECG) for the healthy subject and the cardiac amyloidosis subject.

Table 2 depicts optimized values from PSO framework for the healthy subject and the subject diagnosed with cardiac amyloidosis. The optimized model parameter values including height of the left ventricle, the one or more active pressure components and the one or more passive pressure components specific to the left ventricle ($h_{lv}$, $a_{lv}$, $b_{lv}$) returned against the target values are also mentioned in the table 2. The cardiac hemodynamic model was personalized with the optimized parameter values returned by PSO framework for both healthy subject and the subject suffering from cardiac amyloidosis. For the cardiac amyloidosis disease condition, the LVEDV and LVEDD errors (Table 2) are less than 2% which provides a confidence of successfully replicating the hemodynamics in the presence of diastolic dysfunction, as observed in the cardiac amyloidosis. The correct replication of the disease condition is shown from PV loop parameters.

TABLE 2

PSO Framework performance: Echo data-based personalization.

| Normal | LVEDD ($h_{lv}$ = 11.60) | LVESD ($a_{lv}$ = 1.14) | LVEDV ($b_{lv}$ = 0.03) | LVESV | SV | EF |
|---|---|---|---|---|---|---|
| Target | 4.1 | 2.5 | 104.0 | 45.0 | 59.0 | 56.73 |
| Achieved | 3.66 | 2.54 | 98.87 | 45.21 | 53.66 | 54.27 |
| Error (%) | 10.7 | 1.1 | 4.7 | 0.5 | 5.34 | 4.3 |
| **Cardiac Amyloidosis** | **LVEDD ($h_{lv}$ = 6.27)** | **LVESD ($a_{lv}$ = 11.63)** | **LVEDV ($b_{lv}$ = 0.018)** | **LVESV** | **SV** | **EF** |
| Target | 3.64 | 2.44 | 55.87 | 21.09 | 34.78 | 61.8 |
| Achieved | 3.68 | 2.55 | 57.17 | 24.54 | 32.63 | 57.24 |
| Error (%) | 1.1 | 4.5 | 1.25 | 14.1 | 5.3 | 6.1 |

Figure 8A:
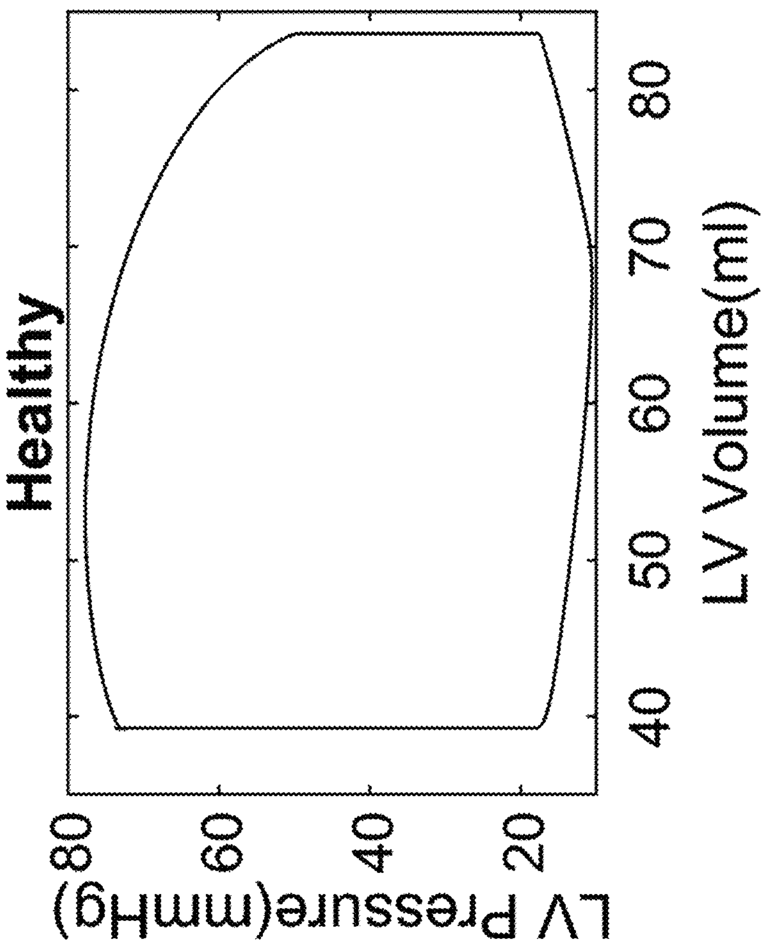
FIGS. 8A and 8B illustrate a left ventricle pressure volume (PV) loop for the healthy subject and the subject diagnosed with cardiac amyloidosis, according to some embodiments of the present disclosure.
Figure 8B:
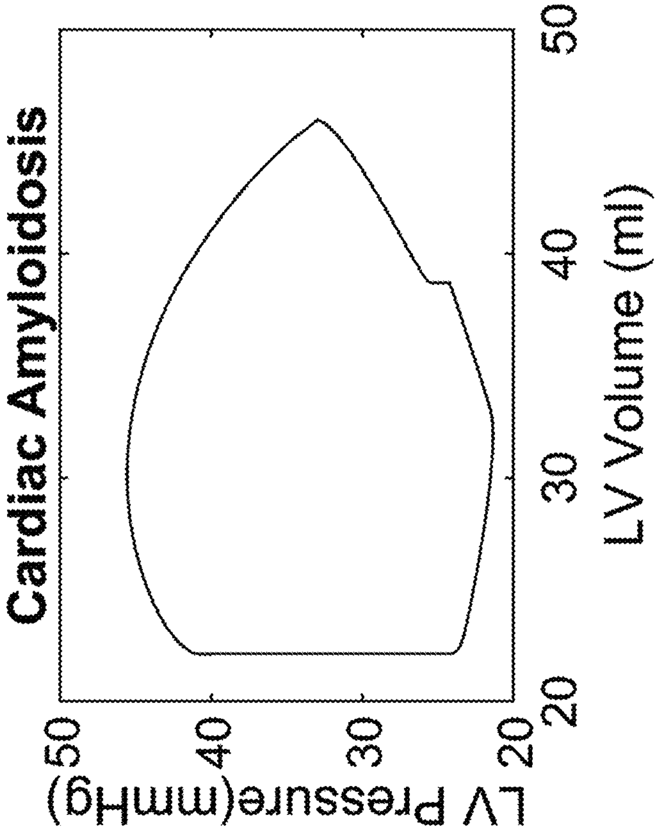

FIGS. 8A and 8B illustrate the left ventricle pressure volume (PV) loop for the healthy subject and the subject diagnosed with cardiac amyloidosis, according to some embodiments of the present disclosure. The left ventricle pressure volume (LV PV) loop and loop derived parameters were computed for both the personalized models. The left ventricle (LV) loop has 4 distinct phases corresponding to different actions during cardiac cycle. Phase 1 represents isovolumetric relaxation followed by ventricular filling phase (phase 2). The volume at end of this phase is the end diastolic volume (EDV). Then is the isovolumetric contraction (phase 3) followed by ventricular ejection (phase 4), volume at end of this phase is the end systolic volume (ESV). PV loops are shown in FIGS. 8A and 8B. Compared to the healthy PV loop, there is an evident change in the shape of the cardiac amyloidosis PV loop, mostly in phase 2 and 3, showing elevated end diastolic pressure and diastolic dysfunction, a signature feature of the cardiac amyloidosis that is well captured from the developed personalized cardiac hemodynamic model. Two important metrics derived from LV PV loop are end systolic pressure volume ratio (ESPVR) which is a surrogate for cardiac elastance and end diastolic pressure volume ratio (EDPVR), representing cardiac muscle stiffness or compliance. These metrics are calculated from the slope around ESV and EDV (shown in FIGS. 8A and 8B). Elevated EDPVR indicates reduced left ventricular compliance, which is a marker for the cardiac amyloidosis.

Figure 9A:
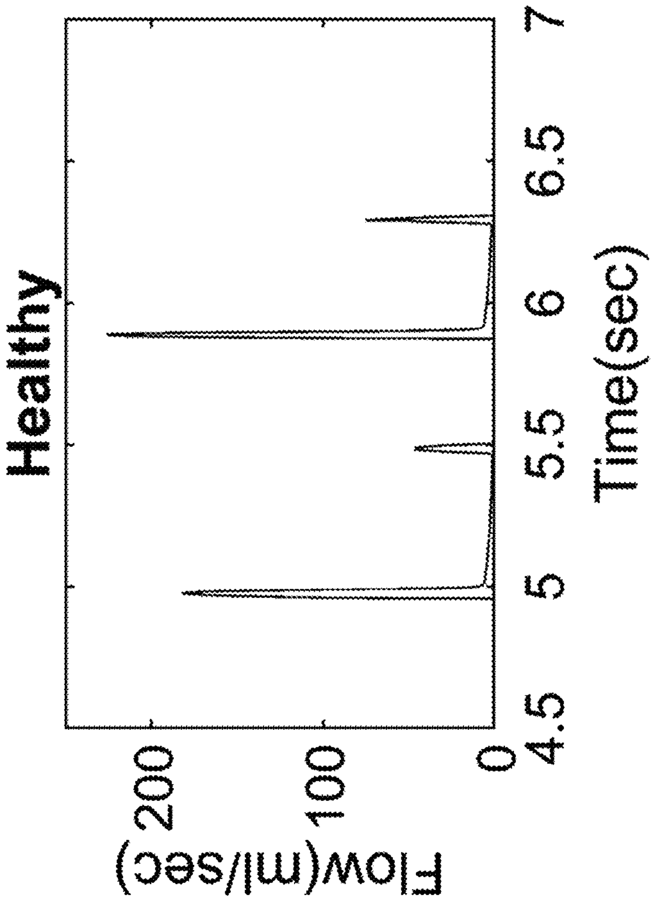
FIGS. 9A and 9B illustrate blood flow across mitral valve for the healthy and the subject diagnosed with cardiac amyloidosis, according to some embodiments of the present disclosure.
Figure 9B:
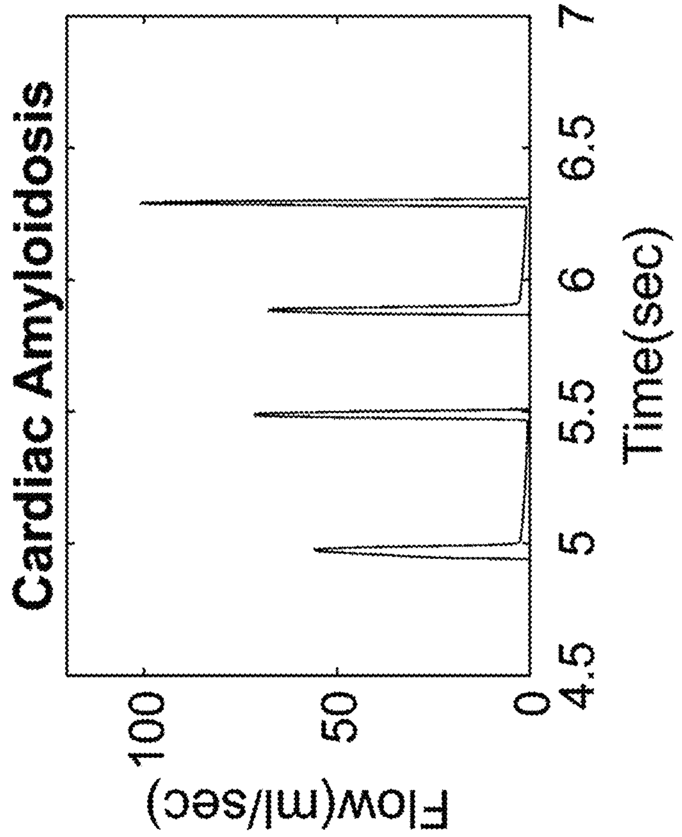

FIGS. 9A and 9B illustrate blood flow across mitral valve for the healthy subject and the subject diagnosed with cardiac amyloidosis, according to some embodiments of the present disclosure. Flow through mitral valve has two peaks, one during early diastolic phase, referred as 'E-wave' and the other is the 'A' wave which is formed due to atrial contraction. E/A ratio is a standard metric reported in Echo data to characterize valve function. In normal condition, E wave>A wave and E/A ratio is greater than 1, as captured in the healthy mitral flow simulation (depicted in the FIGS. 9A and 9B). The echo report of the cardiac amyloidosis subject had E/A ratio of 0.84, indicating A wave>E wave. The simulated mitral flow for the subject with the cardiac amyloidosis captures the altered flow pattern indicating the effectiveness of the personalization framework. Table 3 depicts additional clinical metric derived from the personalized cardiac hemodynamic model. Blood pressure (BP) simulated for the cardiac amyloidosis shows hypotension trend as indicated in medical data of the subject (known in the art). As discussed earlier, the metric EDPVR for amyloidosis shows elevated value, indicating diastolic dysfunction. E/A ratio also indicates impaired filling in LV for amyloidosis. The cardiac hemodynamic model generates cardiac parameters, for both healthy subject and the subject diagnosed with cardiac amyloidosis were consistent with earlier published clinical and experimental data. Although the PSO framework is tested on the one or more model parameters specific to the left ventricle, the same (proposed) methodology can be used to optimize other cardiac chambers as well.

TABLE 3

Additional clinical metric from personalized cardiac hemodynamic model

| Case | HR | BP | ESPVR | EDPVR | E/A |
|---|---|---|---|---|---|
| Normal | 68 | 70/120 | 1.95 | 0.25 | 2.6 |
| Cardiac Amyloidosis | 72 | 50/85 | 1.81 | 0.77 | 0.78 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Existing models for personalized hemodynamic modelling use CT/MRI data that generally capture patient specific estimations. Even though such models can estimate cardiac metrics non-invasively, they are very computationally expensive. The embodiments of present disclosure herein address unresolved problem(s) of improving model parameter optimization and seamless integration of clinical data with computational model required for personalized model development. The embodiment thus provides an optimization framework to personalize parameters of a lumped hemodynamic model using minimal non-invasive clinical data. The cardiac hemodynamic model is personalized using only echocardiogram (ECG) and echo data. The proposed optimization framework is easily scalable to include other chamber parameters. Personalized cardiac hemodynamic model of the present disclosure has been validated against the healthy subject and the subject suffering from a specific disease condition of cardiac amyloidosis. For both the cases, the personalized cardiac hemodynamic model was able to replicate cardiac conditions that match closely with medical data. The system can facilitate clinical use of subject specific model or personalized model that create a virtual e-patient. Such personalized cardiac digital twin could perform predictive modelling and aid in pre-surgical planning, planning for cardiac rehabilitation, generate tailored treatment plan or used as an accelerator for cardiac drug testing.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:

receiving, via one or more hardware processors, (i) one or more model parameters specific to a left ventricle from a cardiac hemodynamic model, wherein the one or more model parameters specific to the left ventricle comprises height of the left ventricle ($h_{lv}$), one or more active pressure components ($a_{lv}$), one or more passive pressure components ($b_{lv}$) and one or more compliance parameters $C_{lv}$, and wherein the cardiac hemodynamic model is driven using an echocardiogram (ECG) data specific to a subject, and (ii) a first set of values corresponding to one or more input parameters from an echo data specific to the subject, wherein the one or more input parameters comprises an end systolic diameter, an end diastole diameter, an end systolic volume and an end diastolic volume specific to the left ventricle;

estimating, via the one or more hardware processors, a second set of values corresponding to (i) the height of the left ventricle ($h_{lv}$) using the first set of values corresponding to the one or more input parameters, which is represented by an equation—

$$d_{lv} = \sqrt{\frac{6V_i}{4\pi K_{lv} h_{lv}}}$$

wherein, $K_{lv}$ is a scale factor which is dependent on geometry of the left ventricle, $V_i$ refers to a volume at any instance in a cardiac cycle, and wherein the height of the left ventricle $h_{lv}$ is dependent on the volume of the left ventricle $V_{lv}$ at any instance in a cardiac cycle which is represented by $$V_{lv} = K_{lv}\frac{4}{3}\pi h_{lv}\frac{d_{lv}^2}{2},$$

and ii) the one or more active pressure components ($a_{lv}$) and the one or more passive pressure components ($b_{lv}$) using the first set of values corresponding to the one or more input parameters, wherein a cardiac chamber pressure of the left ventricle $P_{lv}$ comprising an active filling pressure phase (a) and a passive pressure phase (p) is expressed as $P_{lv}=P_{lv}a+P_{lv}p$, and wherein the passive pressure phase (p) for the one or more active pressure components ($a_{lv}$) and the one or more passive pressure components ($b_{lv}$) is represented by an equation—

$$P_{lv}a = E_{lv}\left(K_{lv}\frac{4}{3}\pi h_{lv}\frac{d_{lv}^2}{4}\right)$$

$$P_{lv}p = a_{lv}e\left(K_{lv}b_{lv}\frac{2}{3}\pi h_{lv}\frac{d_{lv}^2}{2}\right) - 1$$

wherein E is an elastance, which is a reciprocal of a compliance function pertaining to the cardiac chamber pressure of the left ventricle;

optimizing, via the one or more hardware processors, the estimated second set of values corresponding to the one or more model parameters using a particle swarm optimization (PSO) technique to obtain one or more optimized values, wherein the optimization is performed by comparing the estimated second set of values corresponding to the one or more model parameters with the first set of values corresponding to the one or more input parameters; and selecting, via the one or more hardware processors, at least a subset of the one or more optimized values corresponding to the one or more model parameters for personalization.

2. A system, comprising:

a memory storing instructions;

one or more communication interfaces; and one or more hardware processors coupled to the memory via the one or more communication interfaces, wherein the one or more hardware processors are configured by the instructions to:

receive (i) one or more model parameters specific to a left ventricle from a cardiac hemodynamic model, wherein the one or more model parameters specific to the left ventricle comprises height of the left ventricle ($h_{lv}$), one or more active pressure components ($a_{lv}$), one or more passive pressure components ($b_{lv}$) and one or more compliance parameters $C_{lv}$, and wherein the cardiac hemodynamic model is driven using an echocardiogram (ECG) data specific to a subject, and (ii) a first set of values corresponding to one or more input parameters from an echo data specific to the subject, wherein the one or more input parameters comprises an end systolic diameter, an end diastole diameter, an end systolic volume and an end diastolic volume specific to the left ventricle;

estimate a second set of values corresponding to (i) the height of the left ventricle ($h_{lv}$) using the first set of values corresponding to the one or more input parameters, which is represented by an equation—

$$d_{lv} = \sqrt{\frac{6V_i}{4\pi K_{lv} h_{lv}}}$$

wherein, $K_{lv}$ is a scale factor which is dependent on geometry of the left ventricle, $V_i$ refers to a volume at any instance in a cardiac cycle, and wherein the $h_{lv}$ of the left ventricle is dependent on the volume of the left ventricle $V_{lv}$ at any instance in a cardiac cycle which is represented by $$V_{lv} = K_{lv}\frac{4}{3}\pi h_{lv}\frac{d_{lv}^2}{2},$$

and (ii) the one or more active pressure components ($a_{lv}$) and the one or more passive pressure components ($b_{lv}$) using the first set of values corresponding to the one or more input parameters, wherein a cardiac chamber pressure $P_{lv}$ comprising an active filling pressure phase (a) and a passive pressure phase (p) is expressed as $P_{lv}=P_{lv}a+P_{lv}p$, and wherein the passive pressure phase (p) for the one or more active pressure components ($a_{lv}$) and the one or more passive pressure components ($b_{lv}$) is represented by an equation—

$$P_{lv}a = E_{lv}\left(K_{lv}\frac{4}{3}\pi h_{lv}\frac{d_{lv}^2}{4}\right)$$

-continued $$P_{lv}p = a_{lv}e\left(K_{lv}b_{lv}\frac{2}{3}\pi h_{lv}\frac{d_{lv}^2}{2}\right) - 1$$

wherein E is an elastance, which is a reciprocal of a compliance function pertaining to the cardiac chamber pressure of the left ventricle $P_{lv}$;

optimize the estimated second set of values corresponding to the one or more model parameters using a particle swarm optimization (PSO) technique to obtain one or more optimized values, wherein the optimization is performed by comparing the estimated second set of values corresponding to the one or more model parameters with the first set of values corresponding to one or more input parameters; and select at least a subset of the one or more optimized values corresponding to the one or more model parameters for personalization.

3. One or more non-transitory machine-readable information storage mediums comprising one or more instructions which when executed by one or more hardware processors cause:

receiving (i) one or more model parameters specific to a left ventricle from a cardiac hemodynamic model, wherein the one or more model parameters specific to the left ventricle comprises height of the left ventricle ($h_{lv}$), one or more active pressure components ($a_{lv}$), one or more passive pressure components ($b_{lv}$) and one or more compliance parameters $C_{lv}$, and wherein the cardiac hemodynamic model is driven using an echocardiogram (ECG) data specific to a subject, and (ii) a first set of values corresponding to one or more input parameters from an echo data specific to the subject, wherein the one or more input parameters comprises an end systolic diameter, an end diastole diameter, an end systolic volume and an end diastolic volume specific to the left ventricle;

estimating a second set of values corresponding to (i) the height of the left ventricle ($h_{lv}$) using the first set of values corresponding to the one or more input parameters, which is represented by an equation—

$$d_{lv} = \sqrt{\frac{6V_i}{4\pi K_{lv}h_{lv}}}$$

wherein, $K_{lv}$ is a scale factor which is dependent on geometry of the left ventricle, $V_i$ refers to a volume at any instance in a cardiac cycle, and wherein the height of the left ventricle $h_{lv}$ is dependent on the volume of the left ventricle $V_{lv}$ at any instance in a cardiac cycle which is represented by $$V_{lv} = K_{lv}\frac{4}{3}\pi h_{lv}\frac{d_{lv}^2}{2},$$

and (ii) the one or more active pressure components ($a_{lv}$) and the one or more passive pressure components ($b_{lv}$) using the first set of values corresponding to the one or more input parameters, wherein a cardiac chamber pressure of the left ventricle $P_{lv}$ further comprising an active filling pressure phase (a) and a passive pressure phase (p) is expressed as $P_{lv}=P_{lv}a+P_{lv}p$, and wherein the passive pressure phase (p) for the one or more active pressure components ($a_{lv}$) and the one or more passive pressure components ($b_{lv}$) is represented by an equation—

$$P_{lv}a = E_{lv}\left(K_{lv}\frac{4}{3}\pi h_{lv}\frac{d_{lv}^2}{4}\right)$$

$$P_{lv}p = a_{lv}e\left(K_{lv}b_{lv}\frac{2}{3}\pi h_{lv}\frac{d_{lv}^2}{2}\right) - 1$$

wherein E is an elastance, which is a reciprocal of a compliance function pertaining to the cardiac chamber pressure of the left ventricle;

optimizing the estimated second set of values corresponding to the one or more model parameters using a particle swarm optimization (PSO) technique to obtain one or more optimized values, wherein the optimization is performed by comparing the estimated second set of values corresponding to the one or more model parameters with the first set of values corresponding to the one or more input parameters; and selecting at least a subset of the one or more optimized values corresponding to the one or more model parameters for personalization.

* * * * *